United States Patent
Chen et al.

(10) Patent No.: US 10,619,149 B1
(45) Date of Patent: Apr. 14, 2020

(54) FUSANT F001 ABLE TO DIGEST POLYSACCHARIDES

(71) Applicants: NATIONAL PINGTUNG UNIVERSITY OF SCIENCE & TECHNOLOGY, Pingtung County (TW); BiomiXin Co., Ltd., Pingtung County (TW)

(72) Inventors: Yo-Chia Chen, Pingtung County (TW); Rung-Sheng Peng, Pingtung County (TW)

(73) Assignees: NATIONAL PINGTUNG UNIVERSITY OF SCIENCE & TECHNOLOGY, Pingtung County (TW); BIOMIXIN CO., LTD., Pingtung County (TW)

( * ) Notice: Subject to any disclaimer, the term of this patent is extended or adjusted under 35 U.S.C. 154(b) by 0 days.

(21) Appl. No.: 16/532,769

(22) Filed: Aug. 6, 2019

(30) Foreign Application Priority Data

May 8, 2019 (TW) .............................. 108115894 A

(51) Int. Cl.
*C12N 15/03* (2006.01)

(52) U.S. Cl.
CPC .................................... *C12N 15/03* (2013.01)

(58) Field of Classification Search
None
See application file for complete search history.

(56) References Cited

PUBLICATIONS

Genome Announc May 12, 2016;4(3) pp. 1-2) (Year: 2016).*

* cited by examiner

*Primary Examiner* — Padmavathi Baskar
(74) *Attorney, Agent, or Firm* — WPAT, PC

(57) ABSTRACT

A fusant F001 able to digest polysaccharides is formed by protoplast fusion between *Bacillus amyloliquefaciens* and *Bacillus coagulans*. The fusant F001 is deposited at NITE Patent Microorganisms Depositary (NPMD) in Japan with a deposit number NITE BP-02873.

1 Claim, 3 Drawing Sheets

Specification includes a Sequence Listing.

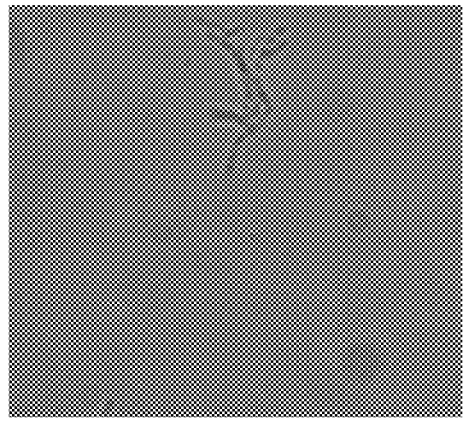
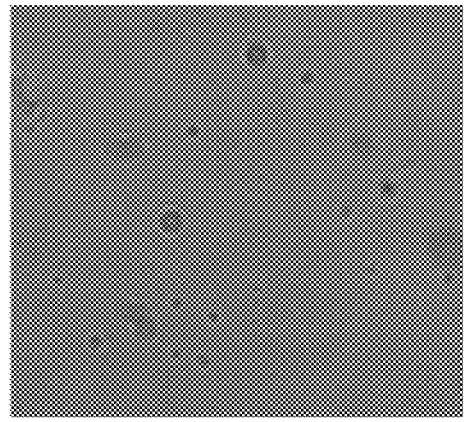
FIG. 1a          FIG. 1b
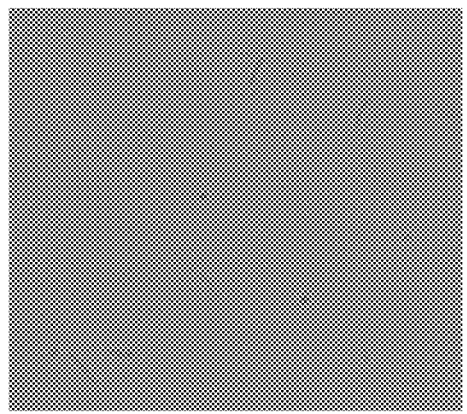
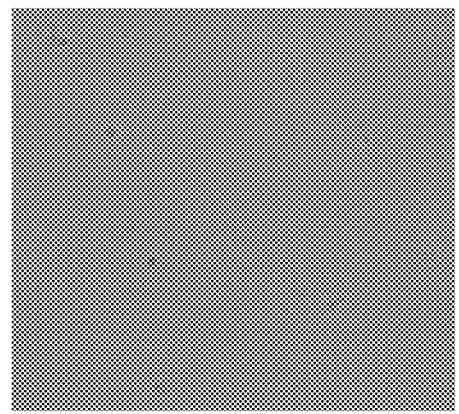
FIG. 1c          FIG. 1d

FIG. 2

FUSANT F001 ABLE TO DIGEST POLYSACCHARIDES

CROSS REFERENCE TO RELATED APPLICATIONS

The application claims the benefit of Taiwan application serial No. 108115894, filed May 8, 2019, the entire contents of which are incorporated herein by reference.

BACKGROUND OF THE INVENTION

1. Field of the Invention

The present invention generally relates to a fusant and, more particularly, to a fusant F001 able to digest polysaccharides.

2. Description of the Related Art

Terrestrial economic animals including livestock and poultry, such as pigs, cows, sheep, deer, chickens, ducks, and geese, can not only produce meat, milk, eggs, fur or other primary livestock products, but also become food or commodity derivatives via cooking or processing.

However, structural polysaccharides, for example, starch, cellulose and xylan, present in the feed are anti-nutritional factors (ANFs) those terrestrial economic animals hard to digest. The ANFs can affect the processes of digestion, absorption and utilization of nutrients. Therefore, the terrestrial economic animals have poor feed conversion rate (FCR), and the economic value of the terrestrial economic animals is reduced. In light of this, it is necessary to provide a fusant able to digest polysaccharides.

SUMMARY OF THE INVENTION

It is therefore an objective of the present invention to provide a fusant F001 able to digest polysaccharides.

An embodiment of the present invention discloses a fusant F001 able to digest polysaccharides. The fusant F001 is formed by protoplast fusion between *Bacillus amyloliquefaciens* and *Bacillus coagulans*. The fusant F001 is deposited at NITE Patent Microorganisms Depositary (NPMD) in Japan with a deposit number NITE BP-02873.

Accordingly, the fusant F001 according to the present invention can effectively digest the anti-nutritional factors (ANF) such as starch, carboxymethyl cellulose (CMC) and xylan. Therefore, the fusant F001 according to the present invention can be used as a feed additive, which is incorporated into the feed for the terrestrial economic animals. With such performance, the terrestrial economic animals can effectively convert the nutrients into primary livestock products and therefore have an improved economic value.

BRIEF DESCRIPTION OF THE DRAWINGS

The present invention will become more fully understood from the detailed description given hereinafter and the accompanying drawings which are given by way of illustration only, and thus are not limitative of the present invention, and wherein:

FIG. 1a depicts a photograph of a *Bacillus amyloliquefaciens* strain before lysozyme treatment.

FIG. 1b depicts a photograph of a protoplast of *B. amyloliquefaciens* formed by lysozyme treatment.

FIG. 1c depicts a photograph of a *Bacillus coagulans* strain before lysozyme treatment.

FIG. 1d depicts a photograph of a protoplast of *B. coagulans* formed by the lysozyme treatment.

FIG. 2 depicts a sequence alignment of 16S rDNA sequences of fusant F001 (upper), the *B. amyloliquefaciens* strain (middle) and the *B. coagulans* strain (lower).

DETAILED DESCRIPTION OF THE INVENTION

Figure 3A:
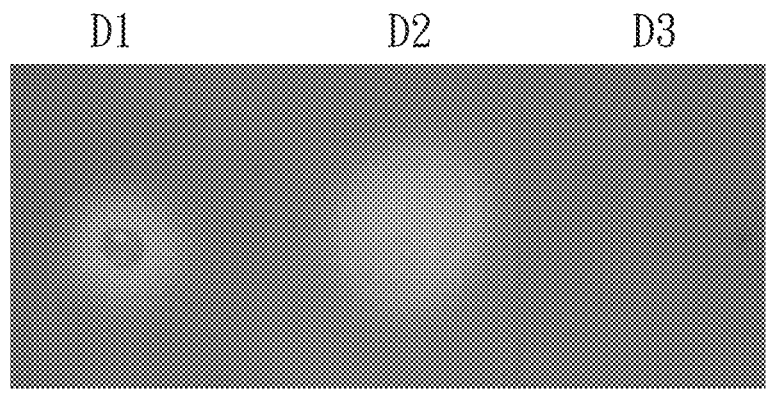
FIG. 3a depicts the growth of the *B. amyloliquefaciens* strain (group D1, left), the fusant F001 (group D2, middle) and the *B. coagulans* strain (group D3, right) on a starch-containing nutrient agar (LB agar).

A fusant F001 able to digest polysaccharides according to the present invention is formed by protoplast fusion between *Bacillus amyloliquefaciens* and *Bacillus coagulans*.

Specifically, cell wall of a *B. amyloliquefaciens* strain, as well as cell wall of a *B. coagulans* strain are degraded by the action of lysozyme to form protoplast of *B. amyloliquefaciens* and a protoplast of *B. coagulans*. In this embodiment, the *B. amyloliquefaciens* strain and the *B. coagulans* strain are respectively added into a protoplast buffer shown in TABLE 1. The degradation of cell wall is carried out at 37° C. for 90 minutes, and the protoplast of *B. amyloliquefaciens* and the protoplast of *B. coagulans* can be obtained.

TABLE 1

| | |
|---|---|
| Sucrose | 0.5 M |
| Tris-HCl | 10 mM |
| MgCl$_2$ | 20 mM |
| Lysozyme (23,500 U/mg) | 0.4 mL |
| | Till 1 L |

The protoplast of *B. amyloliquefaciens* and the protoplast of *B. coagulans* are mixed to form a mixture. The mixture is then added into a fusion buffer. The fusion buffer is an aqueous polyethylene glycol (PEG) solution with a concentration of 40 wt %. The molecular weight of PEG is 6,000. The fusion process is carried out at 37° C. for 10 minutes to obtain plurality of fusants.

The fusant F001 according to the present invention is selected from the plurality of fusants and is the one which grows most rapidly on a nutrient agar (LB agar).

The fusant F001 is deposited at NITE Patent Microorganisms Depositary (NPMD) in Japan with a deposit number NITE BP-02873 (date of original deposit: Feb. 1, 2009). The fusant F001 has a 16S rDNA set forth as SEQ ID NO: 1. The fusant F001 can secrete enzymes such as amylase, cellulase and xylanase, and can digest the polysaccharides such as starch, cellulose and xylan.

To evaluate the fusant F001 according to the present invention can secrete enzymes including amylase, cellulase and xylanase, and can digest the polysaccharides such as starch, cellulose and xylan, the following trials are carried out.

Trial (A).

In trial (A), the *B. amyloliquefaciens* strain and the *B. coagulans* strain are respectively added in to the protoplast buffer including lysozyme. Lysozyme treatment is carried out at 37° C. for 90 minutes. As shown in FIGS. 1a and 1c, before the lysozyme treatment, the *B. amyloliquefaciens* strain and the *B. coagulans* strain appear as rods. After the lysozyme treatment, the *B. amyloliquefaciens* strain and the *B. coagulans* strain converse from rods to round shapes, suggesting that the protoplast of *B. amyloliquefaciens*, as well as the protoplast of *B. coagulans*, is successfully obtained.

After the fusion process, the fusant F001 is selected as the one which grows most rapidly on the nutrient agar (LB agar).

Trial (B).

Figure 2:
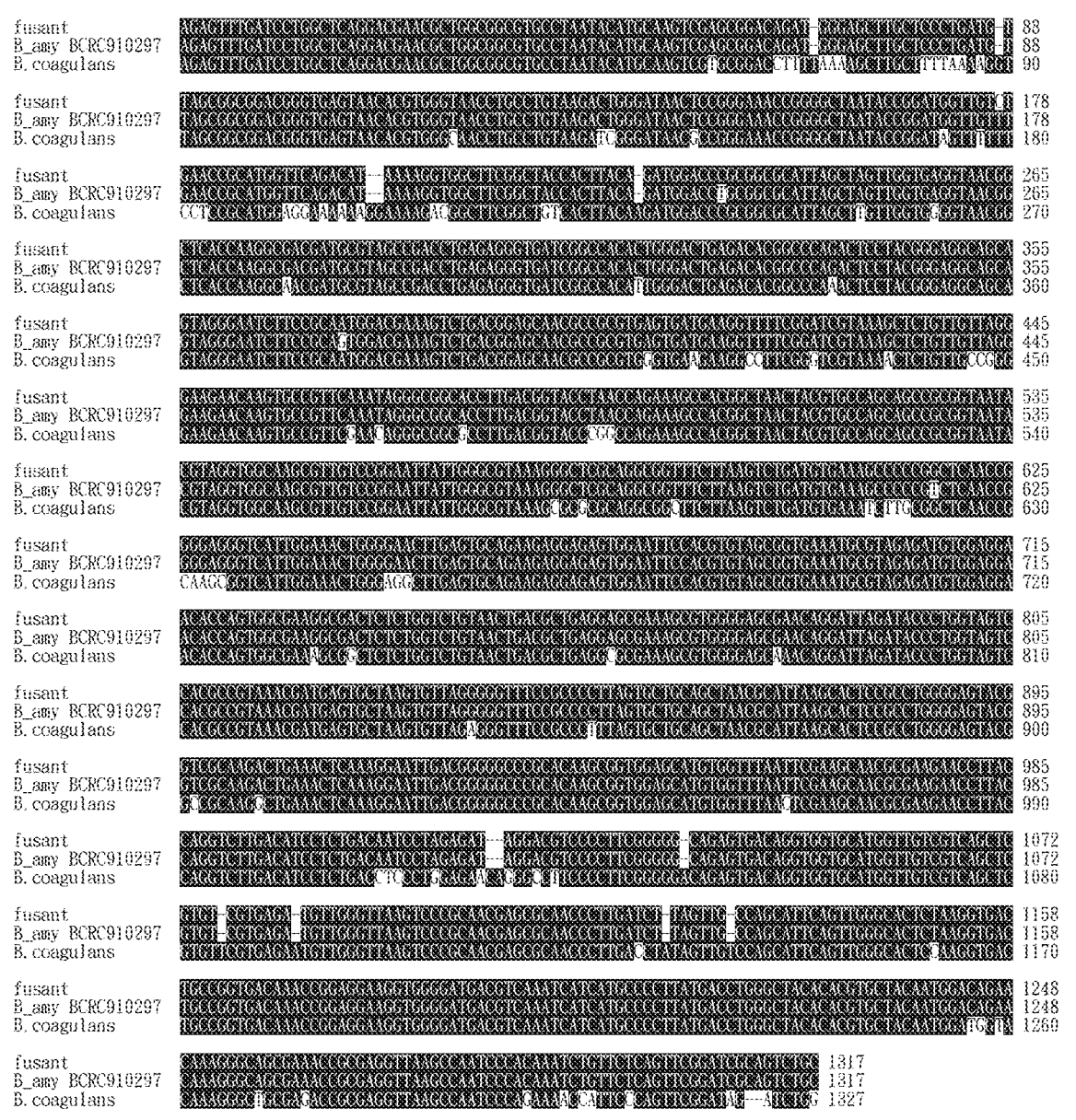

In trial (B), sequence alignment of 16S rDNA sequences of the fusant F001 and parent strains (that is, the *B. amyloliquefaciens* strain and the *B. coagulans* strain) is carried out. As shown in FIG. 2, the 16S rDNA sequence of the fusant F001 differs from either the 16S rDNA sequence of the *B. amyloliquefaciens* strain or the 16S rDNA sequence of the *B. coagulans* strain.

Trial (C).

In trial (C). doubling time (Dt) of the fusant F001 and doubling time of the parent strains (the *B. amyloliquefaciens* strain and the *B. coagulans* strain) are recorded. The result shows that the doubling time (Dt) of the fusant F001 is about 65 minutes, the doubling time (Dt) of the *B. amyloliquefaciens* strain is about 73 minutes, and the doubling time (Dt) of the *B. coagulans* strain is about 214 minutes, suggesting that the fusant F001 has a rapidly growth rate compared to the parent strains (the *B. amyloliquefaciens* strain and the *B. coagulans* strain).

Trial (D).

In trial (D), the *B. amyloliquefaciens* strain (group D1), the fusant F001 (group D2) and the *B. coagulans* strain (group D3) are cultured on a nutrient agar (LB agar) containing 0.5% of starch at 37° C. for 24 hours. The starch-containing nutrient agar (LB agar) is then stained by an iodine solution. As shown in FIG. 3a, a diameter of clear zone of the fusant F001 (group D2) is larger than diameters of clear zones of the parent strains (the *B. amyloliquefaciens* strain, group D1, and the *B. coagulans* strain, group D3), suggesting that the fusant F001 has an improved activity for digesting starch.

Figure 3B:
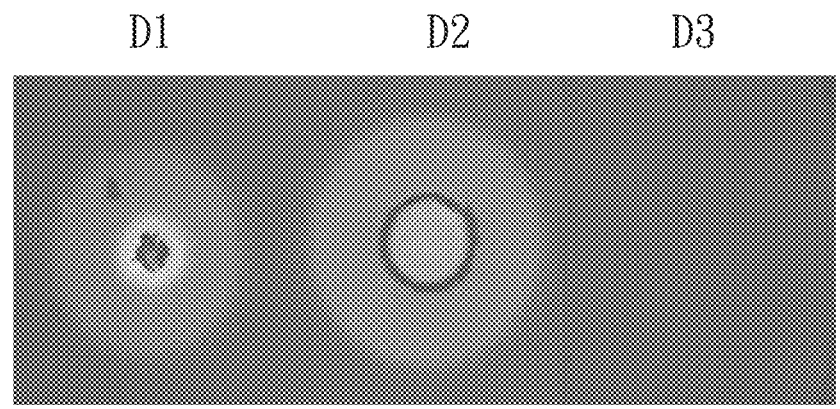
FIG. 3b depicts the growth of the *B. amyloliquefaciens* strain (group D1, left), the fusant F001 *B. coagulans* (group D2, middle) and the *B. coagulans* strain (group D3, right) on a carboxymethyl cellulose (CMC)-containing nutrient agar (LB agar).
Figure 3C:
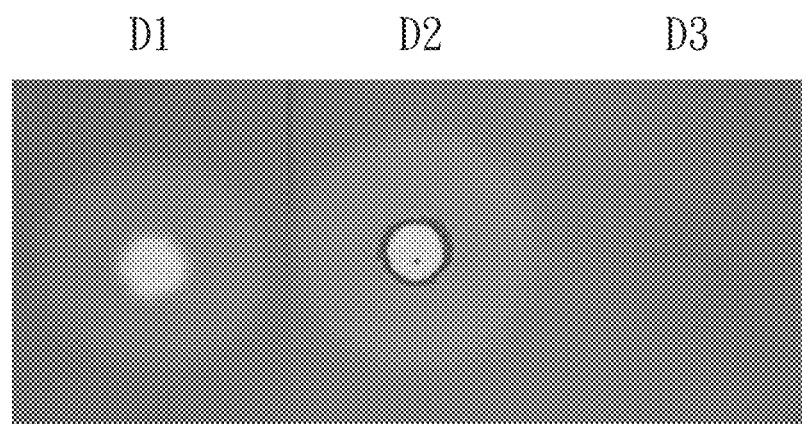
FIG. 3c depicts the growth of the *B. amyloliquefaciens* strain (group D1, left), the fusant F001 *B. coagulans* (group D2, middle) and the *B. coagulans* strain (group D3, right) on a xylan-containing nutrient agar (LB agar).

Moreover, the *B. amyloliquefaciens* strain (group D1), the fusant F001 (group D2) and the *B. coagulans* strain (group D3) are cultured on a nutrient agar (LB agar) containing 0.5% of carboxymethyl cellulose (CMC) or 0.5% of xylan at 37° C. for 24 hours. The CMC-containing nutrient agar (LB agar) or the xylan-containing nutrient agar (LB agar) is stained by congo red. As shown in FIGS. 3b & 3c, a diameter of clear zone of the fusant F001 (group D2) is larger than diameters of clear zones of the parent strains (the *B. amyloliquefaciens* strain, group D1, and the *B. coagulans* strain, group D3), suggesting that the fusant F001 has an improved activity for digesting either carboxymethyl cellulose (CMC) or xylan.

In addition, the *B. amyloliquefaciens* strain (group D1), the fusant F001 (group D2) and the *B. coagulans* strain (group D3) are cultured in a nutrient broth (LB broth) at 37° C. for 24 hours, respectively. A supernatant is obtained by centrifugation, and enzyme activities of amylase, cellulase and xylanase in the supernatants of groups D1-D3 are detected.

TABLE 2

|     | Amylase (U/mL) | Cellulase (U/mL) | Xylanase (U/mL) |
|-----|---------------|------------------|-----------------|
| D1  | 1.3           | 0.3              | 2.0             |
| D2  | 2.3           | 0.6              | 4.2             |
| D3  | 0             | 0                | 0               |

Referring to TABLE 2, regardless of amylase, cellulase and xylanase, the fusant F001 (group D2) has an improved enzyme activity compared to the parent strains (the *B. amyloliquefaciens* strain, group D1, and the *B. coagulans* strain, group D3).

Accordingly, the fusant F001 according to the present invention can effectively digest the anti-nutritional factors (ANF) such as starch, carboxymethyl cellulose (CMC) and xylan. Therefore, the fusant F001 according to the present invention can be used as a feed additive, which is incorporated into the feed for the terrestrial economic animals. With such performance, the terrestrial economic animals can effectively convert the nutrients into primary livestock products and therefore have an improved economic value.

Although the invention has been described in detail with reference to its presently preferable embodiment, it will be understood by one of ordinary skill in the art that various modifications can be made without departing from the spirit and the scope of the invention, as set forth in the appended claims.

What is claimed is:

1. A fusant F001 able to digest polysaccharides, formed by protoplast fusion between *Bacillus amyloliquefaciens* and *Bacillus coagulans*, wherein the fusant F001 is deposited at NITE Patent Microorganisms Depositary (NPMD) in Japan with a deposit number NITE BP-02873.

* * * * *

SEQUENCE LISTING

```
<160> NUMBER OF SEQ ID NOS: 1

<210> SEQ ID NO 1
<211> LENGTH: 1317
<212> TYPE: DNA
<213> ORGANISM: Artificial Sequence
<220> FEATURE:
<223> OTHER INFORMATION: Fusant F001

<400> SEQUENCE: 1
agagtttgat cctggctcag gacgaacgct ggcggcgtgc ctaatacatg caagtcgagc      60
ggacagatgg gagcttgctc cctgatgtta gcggcggacg ggtgagtaac acgtgggtaa     120
cctgcctgta agactgggat aactccggga aaccggggct aataccggat ggttgtctga     180
accgcatggt tcagacataa aaggtggctt cggctaccac ttacagatgg acccgcggcg     240
```

-continued

```
cattagctag ttggtgaggt aacggctcac caaggcgacg atgcgtagcc gacctgagag    300
ggtgatcggc cacactggga ctgagacacg gcccagactc ctacgggagg cagcagtagg    360
gaatcttccg caatggacga aagtctgacg gagcaacgcc gcgtgagtga tgaaggtttt    420
cggatcgtaa agctctgttg ttagggaaga acaagtgccg ttcaaatagg gcggcacctt    480
gacggtacct aaccagaaag ccacggctaa ctacgtgcca gcagccgcgg taatacgtag    540
gtggcaagcg ttgtccggaa ttattgggcg taaagggctc gcaggcggtt tcttaagtct    600
gatgtgaaag cccccggctc aaccggggag ggtcattgga aactgggaa cttgagtgca    660
gaagaggaga gtggaattcc acgtgtagcg gtgaaatgcg tagagatgtg gaggaacacc    720
agtggcgaag gcgactctct ggtctgtaac tgacgctgag gagcgaaagc gtggggagcg    780
aacaggatta gataccctgg tagtccacgc cgtaaacgat gagtgctaag tgttagggg    840
tttccgcccc ttagtgctgc agctaacgca ttaagcactc cgcctgggga gtacggtcgc    900
aagactgaaa ctcaaaggaa ttgacggggg cccgcacaag cggtggagca tgtggtttaa    960
ttcgaagcaa cgcgaagaac cttaccaggt cttgacatcc tctgacaatc ctagagatag   1020
gacgtcccct tcgggggcag agtgacaggt ggtgcatggt tgtcgtcagc tcgtgtcgtg   1080
agatgttggg ttaagtcccg caacgagcgc aaccctgat cttagttgcc agcattcagt   1140
tgggcactct aaggtgactg ccggtgacaa accggaggaa ggtggggatg acgtcaaatc   1200
atcatgcccc ttatgacctg ggctacacac gtgctacaat ggacagaaca aagggcagcg   1260
aaaccgcgag gttaagccaa tcccacaaat ctgttctcag ttcggatcgc agtctgc     1317
```